United States Patent [19]

Bank

[11] Patent Number: 5,136,070
[45] Date of Patent: Aug. 4, 1992

[54] SODIUM BOROHYDRIDE CATALYZED DISPROPORTIONATION OF CYCLOORGANOSILANES

[75] Inventor: Howard M. Bank, Freeland, Mich.

[73] Assignee: Dow Corning Corporation, Midland, Mich.

[21] Appl. No.: 812,297

[22] Filed: Dec. 23, 1991

[51] Int. Cl.$^5$ ............................................... C07F 7/08
[52] U.S. Cl. .................................................... 556/469
[58] Field of Search ........................................ 556/469

[56] References Cited

U.S. PATENT DOCUMENTS

| | | | |
|---|---|---|---|
| 2,627,451 | 2/1953 | Erickson et al. | 556/469 X |
| 2,735,861 | 2/1956 | Erickson et al. | 556/469 |
| 2,746,981 | 5/1956 | Wagner | 556/469 |

FOREIGN PATENT DOCUMENTS 263189  4/1987  Japan .

Primary Examiner—Paul F. Shaver
Attorney, Agent, or Firm—William F. Boley

[57] ABSTRACT

The present invention is a process for the disproportionation of cycloorganosilanes using sodium borohydride as a catalyst. The process requires the presence of a hydrogen and a cycloorgano-substituent bonded to a single silicon atom, where the cycloorgano-substituent is a radical selected from a group consisting of aryls, substituted aryls, cycloalkyls, and substituted cycloalkyls. The present process is especially useful as a continuous process for the disproportionation of phenyldichlorosilane to diphenyldichlorosilane and dichlorosilane.

14 Claims, No Drawings

SODIUM BOROHYDRIDE CATALYZED DISPROPORTIONATION OF CYCLOORGANOSILANES

BACKGROUND OF INVENTION

The present invention is a process for the disproportionation of cycloorganosilanes using sodium borohydride as a catalyst. The process requires the presence of a hydrogen and a cycloorgano-substituent bonded to a single silicon atom, where the cycloorgano-substituent is a radical selected from a group consisting of aryls, substituted aryls, cycloalkyls, and substituted cycloalkyls.

The use of a catalyst to effect the disproportionation of arylsilanes is known. For Example, Wagner, U.S. Pat. No. 2,746,981, issued May 22, 1956, teaches the preparation of diaryldichlorosilanes by heating monoaryldichlorosilanes in the presence of a Friedel-Crafts type catalyst taken from the group consisting of aluminum or boron chloride.

Japanese Patent No. 263189, published in 1987, teaches a process where arylboranes for example triphenylborane, is used to catalyze the disproportionation of aryldihalosilanes under conditions of reduced pressure. Running the process at reduced pressure is reported to increase the yield of diarylhalosilane.

The present process describes the use of sodium borohydride as a catalyst for the disproportionation of cycloorganosilanes. The sodium borohydride is essentially insoluble in the process, making it especially useful as a fixed-bed in a continuous process. Cycloorganosilanes prepared by the present process are useful, for example, for the preparation of siloxane polymers and for the preparation of release coatings for paper.

SUMMARY OF INVENTION

The present invention is a process for the disproportionation of cycloorganosilanes using sodium borohydride as a catalyst. The process requires the presence of a hydrogen and a cycloorgano substituent bonded to a single silicon atom, where the cycloorgano-substituent is a radical selected from a group consisting of aryls, substituted aryls, cycloalkyls, and substituted cycloalkyls. The present process is especially useful as a continuous process for the disproportionation of phenyldichlorosilane to diphenyldichlorosilane and dichlorosilane.

DESCRIPTION OF INVENTION

The present invention is a process for the disproportionation of cycloorganosilanes. The process comprises (A) forming a mixture comprising cycloorganosilanes of formula

$$R_aR^1_bH_cSiX_{4-a-b-c}, \quad (1)$$

and sodium borohydride catalyst where concentration of the sodium borohydride catalyst is sufficient to increase the rate of disproportionation of the cycloorganosilanes;

(B) heating the mixture to a temperature within a range of about 100° C. to 250° C.; and (C) recovering product silanes of formula

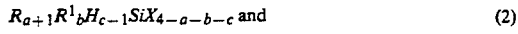

$$R_{a+1}R^1_bH_{c-1}SiX_{4-a-b-c} \text{ and} \quad (2)$$

$$R_{a-1}R^1_bH_{c+1}SiX_{4-a-b-c}; \quad (3)$$

where each R is independently selected from a group consisting of aryls, substituted aryls cycloalkyls of four to 20 carbon atoms, and substituted cycloalkyls of four to 20 carbon atoms, $R^1$ is selected from a group consisting of alkyls of one to 20 carbon atoms, X is a halogen selected from a group consisting of bromine, chlorine and iodine, a=1, 2, or 3, b=0, 1, or 2, c=1, 2, or 3, and a+b+c=2, 3, or 4.

Cycloorganosilanes which can be disproportionated by the present process are described by formula (1). The cycloorganosilane can contain one, two, or three R substituents, where each R is a radical independently selected from a group consisting of aryls, substituted, aryls, cycloalkyls or four to 20 carbon atoms, and substituted cycloalkyls of four to 20 carbon atoms. By "substituted aryls" and "substituted cycloalkyls" it is meant that one or more of the carbons forming the cyclic ring is substituted with a substituent selected from a group consisting of alkyls of one to 20 carbon atoms; haloalkyls of one to 20 carbon atoms; and halogens. The halogen can be bromine, chlorine, fluorine, and iodine. Preferred is when the halogen is chlorine or fluorine. The radical R can be, for example, phenyl, biphenyl, naphthyl, tolyl, xylyl, isopropylphenyl, chlorophenyl, dichlorophenyl, fluorophenyl, cyclopentyl, cyclohexyl, cycloheptyl, and methylcyclohexyl. Preferred is when R is selected from a group consisting of phenyl, cyclopentyl, and cyclohexyl.

The cycloorganosilane can contain zero, one, or two substituents $R^1$, where $R^1$ is an alkyl radical of one to 20 carbon atoms. The radical $R^1$ can be, for example, methyl ethyl, propyl, isopropyl butyl, tert-butyl, and decyl. Preferred is when $R^1$ is methyl.

The cycloorganosilane must contain at least one hydrogen bonded to the silicon atom and can contain a maximum of three hydrogen atoms bonded to the silicon atom. It is preferred that the cycloorganosilane contain one hydrogen bonded to the silicon atom.

The cycloorganosilane can contain zero, one, or two halogens, X, where X is selected from a group consisting of bromine, chlorine, and iodine. The preferred halogen, for X, is chlorine.

The cycloorganosilane can be, for example, phenyldichlorosilane, phenylchlorosilane, phenyldibromosilane, phenyldiiodosilane, tolyldichlorosilane, chlorophenyldichlorosilane, methylphenylchlorosilane, ethylphenylchlorosilane, triphenylsilane, phenylsilane, cyclopentyldichlorosilane, cyclohexyldichlorosilane, cyclohexylmethylchlorosilane, and cycloheptyldichlorosilane.

Sodium borohydride is added to the process as a catalyst. The concentration of sodium borohydride added to the process can be any concentration sufficient to increase the rate of disproportionation of the cycloorganosilane. The sodium borohydride is added to the process as a solid in the form of, for example, powder, chips, flakes, granules, and pellets. Preferred is when the sodium borohydride has a particle size greater then about 100 microns. More preferred is when the sodium borohydride has a particle size within a range of about 1 mm to 12 mm in diameter.

The present process can be run as a continuous process or as a batch process in standard type reactors for running such processes. Since the sodium borohydride is present in the process as a solid, it is possible to form, for example, a packed-bed, fluidized-bed, or stirred-bed of the sodium borohydride and pass the cycloorganosilanes through the bed to effect disproportionation. When the process is run as a batch process, a concentration of sodium borohydride within a range of about 0.05 to 10 weight percent of the weight of the cycloorganosilanes added to the process is preferred. More preferred is a concentration of sodium borohydride within a range of about 0.5 to 2.0 weight percent of the cycloorganosilanes added to the process.

The mixture comprising the cycloorganosilane and sodium borohydride catalyst is heated to a temperature within a range of about 100° C. to 250° C. A preferred temperature is within a range of about 150° C. to 200° C. The most preferred temperature in within a range greater than about 170° C. to 200° C.

The length of time required to heat the mixture to effect disproportionation of the cycloorganosilanes will depend upon such factors as, for example, the temperature of the process and the particular cycloorganosilanes employed in the process. In general heating times of about 0.5 minutes to 18 hours are considered useful. Preferred are heating times of about 15 minutes to one hour.

The present process can be run under standard, reduced, or elevated pressures. Preferred is when the process is run at reduced pressure. By "reduced pressure" is meant a pressure less than a standard pressure of about 760 mmHg. In the described process, two cycloorganosilane molecules disproportionate effecting an exchange of an R substituent of one cycloorganosilane for a hydrogen on the silicon atom of the other cycloorganosilane. The result of this disproportionation reaction is a product silane molecule containing an added R substituent and a second lower-boiling product silane containing an additional hydrogen. The inventors believe that the cycloorganosilanes and product silanes form an equilibrium mixture. Therefore by removing the second lower-boiling silane as it is formed, process yield of the silane products containing an added R substituent is improved.

Product silanes of formula (2) and formula (3) are recovered from the process. The method of recovery of the product silanes depends upon whether the process is run as a continuous process or as a batch process. When the process is run as a continuous process, recovery of the product silanes can be effected by, for example, distillation. When the process is run as a batch process, separation of the solid sodium borohydride from the product silanes can be effected by standard methods for separating solids from liquids, for example, filtration or settling. The separated liquid can then be distilled to recover product silanes.

The product silanes can be, for example, diphenyldichlorosilane, triphenylchlorosilane, diphenyldibromosilane, diphenyldiiodosilane, ditolyldichlorosilane, di(chlorophenyl)dichlorosilane, methyldiphenylchlorosilane, ethyldiphenylchlorosilane, dichlorosilane, diphenylchlorosilane, methylchlorosilane, ethylchlorosilane, diphenylsilane, tetraphenylsilane, dicyclopentyldichlorosilane, dicyclohexyldichlorosilane, dicyclohexylmethylchlorosilane, and dicycloheptyldichlorosilane.

The following examples are provided to illustrate the present invention. These examples are not intended to limit the present claims.

EXAMPLE 1

Various materials were evaluated for their ability to catalyze the disproportionation of phenyldichlorosilane. The evaluation was conducted in sealed, 8 mm by 25 cm, Pyrex Brand tubes. Prior to sealing and use, the Pyrex tubes were dried in an oven at 140° C. for 16 hours. The tubes were then removed from the oven, purged with argon, and placed in an argon-purged bag, where 2.0 mL of phenyldichlorosilane was added to each tube. The materials tested as catalyst were sodium borohydride ($NaBH_4$), Morton Thiokol, Danvers, Mass.; calcium hydride ($CaH_2$), Fisher Scientific Company, Fair Lawn, N.J.; and decaborane ($B_{10}H_{14}$), Aldrich, Milwaukee, Wis. The sodium borohydride was received in the form of 8 mm pellets, which were crushed into a coarse particulate mixture prior to addition to the process. The concentration of materials tested as catalyst are presented in table 1. The concentration is presented as the weight of material added per 2.0 mL of phenyldichlorosilane. The tubes were sealed and placed in a tube furnace for one hour at 170° C. At the end of one hour of heating, the tubes were cooled and the contents analyzed by gas liquid chromotography using a flame ionization detector (GLC-FID). The results are presented in Table 1 as the percent area (% Area) under the GLC-FID trace for each of the listed compounds.

TABLE 1

| Disproportionation of Phenyldichlorosilane at 170° C. | | | | |
|---|---|---|---|---|
| | GLC-FID % Area | | | |
| Catalyst | $HSiCl_3/C_6H_6$ | $PhH_2SiCl$ | $PhHSiCl_2$ | $Ph_2SiCl_2$ |
| — | 6.3 | 0.0 | 92.9 | 0.0 |
| 0.025 g $NaBH_4$ | 14.2 | 1.5 | 31.2 | 46.6 |
| 0.042 g $CaH_2$ | 0.0 | 0.0 | 98.8 | 0.0 |
| 0.031 g $B_{10}H_{14}$ | 0.1 | 0.0 | 96.0 | 0.0 |

EXAMPLE 2

The ability of sodium borohydride to catalyze the thermal disproportionation of methylphenylchlorosilane was evaluated. The evaluation was conducted in glass tubes under an argon blanket as described in Example 1. To a glass tube was added 2.0 mL of methylphenylchlorosilane and 0.028 g of a crushed pellet of sodium borohydride (As described in Example 1). A control tube containing methylphenylchlorosilane, but no sodium borohydride, was also run. The sealed tubes were heated in a tube furnace at 170° C. for one hour. At the end of the one hour heating period, the tubes were cooled and the contents analyzed by GLC-FID. The results are presented in Table 2 as the percent area under the GLC-FID trace for each of the listed compounds.

TABLE 2

| Sodium Borohydride Catalyzed Disproportionation of Methylphenylchlorosilane | | | | | | |
|---|---|---|---|---|---|---|
| | GLC-FID % Area | | | | | |
| Cat. | $MeHSiCl_2$ | $PhMeSiH_2$ | $PhMeHSiCl$ | $PhMeSiCl_2$ | $(PhMeHSi)_2O$ | $Ph_2MeSiCl$ |
| — | 0.0 | 0.0 | 77.1 | 0.0 | 20.9 | 0.0 |

TABLE 2-continued
Sodium Borohydride Catalyzed Disproportionation of Methylphenylchlorosilane

| Cat. | GLC-FID % Area | | | | | |
|---|---|---|---|---|---|---|
| | MeHSiCl$_2$ | PhMeSiH$_2$ | PhMeHSiCl | PhMeSiCl$_2$ | (PhMeHSi)$_2$O | Ph$_2$MeSiCl |
| NaBH$_4$ | 3.5 | 4.1 | 9.0 | 1.1 | 39.9 | 28.0 |

EXAMPLE 3

The ability of sodium borohydride to catalyze the disproportionation of cyclohexyldichlorosilane was evaluated. The evaluation was conducted in glass tubes under an argon blanket as described in Example 1. To a glass tube was added 2.0 mL of cyclohexyldichorosilane and 0.027 g of a crushed pellet of sodium borohydride (As described in Example 1). A control tube containing cyclohexyldichorosilane, but no sodium borohydride, was also run. The sealed tubes were heated in a tube furnace at 170° C. for one hour. At the end of the one hour heating period, the tubes were cooled and the contents analyzed by GLC-FID. The results are presented in Table 3 as the percent area under the GLC-FID trace for each of the listed compounds.

TABLE 3
Sodium Borohydride Catalyzed Disproportionation of Cyclohexyldichlorosilane

| Catalyst | GLC-FID % Area | | | |
|---|---|---|---|---|
| | C$_6$H$_{12}$ | (C$_6$H$_{11}$)SiH$_2$Cl | (C$_6$H$_{11}$)SiHCl$_2$ | (C$_6$H$_{11}$)$_2$SiCl$_2$ |
| — | 0.0 | 0.0 | 96.5 | 0.3 |
| NaBH$_4$ | 1.3 | 0.8 | 89.1 | 1.0 |

What is claimed is:

1. A process for disproportionation of cycloorganosilanes, the process comprising
   (A) forming a mixture comprising cycloorganosilanes of formula $R_aR^1{}_bH_cSiX_{4-a-b-c}$, and sodium borohydride catalyst, where concentration of the sodium borohydride catalyst is sufficient to increase the rate of disproportionation of the cycloorganosilanes;
   (B) heating the mixture to a temperature within a range of about 100° C. to 250° C.; and
   (C) recovering product silanes of formula $R_{a+1}R^1{}_bH_{c-1}SiX_{4-a-b-c}$ and $R_{a-1}R^1{}_bH_{c+1}SiX_{4-a-b-c}$;

where each R is independently selected from a group consisting of aryls, substituted aryls, cycloalkyls of one to 20 carbon atoms, and substituted cycloalkyls of one to 20 carbon atoms, R$^1$ is selected from a group consisting of alkyls of one to 20 carbon atoms. X is a halogen selected from a group consisting of bromine, chlorine and iodine, a=1, 2, or 3, b=0, 1, or 2, c=1, 2, or 3, and a+b+c=2, 3, or 4.

2. A process according to claim 1, where X is chlorine.

3. A process according to claim 1, where R is selected from a group consisting of phenyl, cyclopentyl, and cyclohexyl.

4. A process according to claim 1, where R$^1$ is methyl.

5. A process according to claim 1, where c is one.

6. A process according to claim 1, where the sodium borohydride catalyst is a particulate having a particle size within a range of about 1 mm to 12 mm in diameter.

7. A process according to claim 1, where the process is run as a continuous process.

8. A process according to claim 1, where the process is run as a batch process and the concentration of the sodium borohydride catalyst is within a range of about 0.05 to 10 weight percent of the cycloorganosilanes added to the process.

9. A process according to claim 1, where the temperature is within a range of about 150° C. to 200° C.

10. A process according to claim 1, where the temperature is within a range greater than about 170° C. to 200° C.

11. A process according to claim 1, where the mixture is heated for about 15 minutes to one hour.

12. A process according to claim 1, where the process is run at reduced pressure and product silanes of the formula $R_{a-1}R^1{}_bH_{c+1}SiX_{4-a-b-c}$ are removed from the process as they are formed.

13. A process according to claim 1, where the product silanes are selected from a group consisting of diphenyldichlorosilane and methyldiphenylchlorosilane.

14. A process according to claim 1, where the product silanes are selected from a group consisting of dicyclopentyldichlorosilane and dicyclohexyldichlorosilane.

* * * * *